United States Patent [19]
Holt

[11] Patent Number: 5,457,260
[45] Date of Patent: Oct. 10, 1995

[54] CONTROL PROCESS FOR SIMULATED MOVING ADSORBENT BED SEPARATIONS

[75] Inventor: Randall E. Holt, Elgin, Ill.

[73] Assignee: UOP, Des Plaines, Ill.

[21] Appl. No.: 173,844

[22] Filed: Dec. 27, 1993

[51] Int. Cl.$^6$ .................................................. C07C 7/12
[52] U.S. Cl. ..................... 585/820; 585/821; 208/DIG. 1
[58] Field of Search ..................................... 585/820, 821; 208/DIG. 1

[56] References Cited

U.S. PATENT DOCUMENTS

| | | | |
|---|---|---|---|
| 2,985,589 | 5/1961 | Broughton | 210/34 |
| 3,201,491 | 8/1965 | Stine et al. | 585/821 |
| 3,205,166 | 9/1965 | Ludlow et al. | 585/821 |
| 3,268,604 | 8/1966 | Boyd | 585/821 |
| 3,268,605 | 8/1966 | Boyd | 585/821 |

FOREIGN PATENT DOCUMENTS 2050108  3/1992  Canada .

OTHER PUBLICATIONS

Mowry, J. R. in *Handbook of Petroleum Refining Procsses;* Meyers, R. A. Ed.; McGraw–Hill: New York, 1986; pp. 8–79 to 8–99.

*Primary Examiner*—Sharon A. Gibson
*Assistant Examiner*—Walter D. Griffin
*Attorney, Agent, or Firm*—Thomas K. McBride; Eugene I. Snyder

[57] ABSTRACT

A process of continuously controlling at least one characteristic of a simulated moving adsorbent bed separation process has been developed. The characteristics controlled may be the purity or the recovery of the component of interest. The process involves measuring the concentration of the components in the pumparound or pusharound stream, calculating the value of the characteristic, and making required adjustments to operating variables according to an algorithm which relates changes in the value of the characteristic to the changes in the concentrations of the components resulting from changes in the operating variables. The process is unique in that the necessary quantity of data to control the separation is rapidly generated, thereby providing increased efficiency, precision and accuracy.

8 Claims, 1 Drawing Sheet

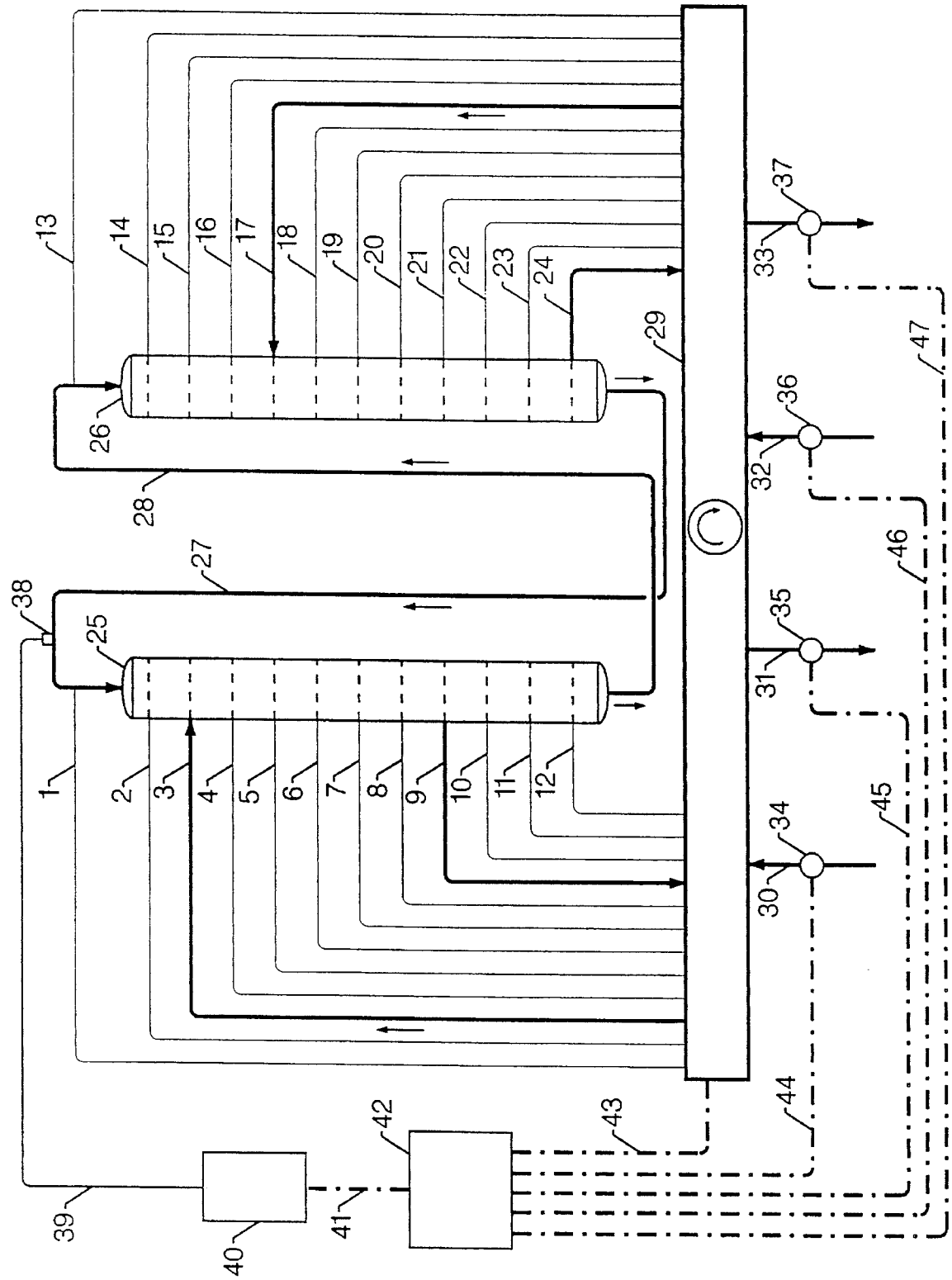

CONTROL PROCESS FOR SIMULATED MOVING ADSORBENT BED SEPARATIONS

BACKGROUND OF THE INVENTION

Continuous separation processes for the selective adsorption of one component or group of components from a mixture are common in industry. Examples of such processes are the separation of linear paraffins from branched-chain and cyclic hydrocarbons, olefins from paraffins, para-cresol or meta-cresol from cresol isomers, para-cymene from oymene isomers, 1-butene from a mixture of paraffins and olefins which contain four carbon atoms, fructose and glucose from mixtures thereof, para-xylene from xylene isomers, ethylbenzene from aromatic isomers containing eight carbon atoms, cyclic hydrocarbons and olefins from paraffins and others.

Generally, such separation processes use a solid adsorbent which preferentially retains the component or group of components of interest in order to separate them from the rest of the mixture. There are a wide variety of solid adsorbents available, and each separation application may require a different solid adsorbent. For example, the separation of linear paraffins from branched-chain or cyclic hydrocarbons typically requires a molecular sieve commonly known as 5A, while another application would require a completely different adsorbent. Often, the solid adsorbent is in the form of a simulated moving bed, where the bed of solid adsorbent is held stationary, and the locations at which the various streams enter and leave the bed are periodically moved. The adsorbent bed itself is usually a succession of fixed sub-beds, and different applications may require differing numbers of sub-beds. The shift in the locations of liquid input and output in the direction of the fluid flow through the bed simulates the movement of the solid adsorbent in the opposite direction. Commercially, moving the locations of liquid input and output is accomplished by a fluid directing device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a specified time period, called the step time, the rotary valve advances one index and redirects the liquid inputs and outputs to the distributors immediately adjacent and downstream of the previously used distributors. Each advancement of the rotary valve to a new valve position is generally called a valve step, and the completion of all the valve steps is called a valve cycle. The step time is uniform for each valve step in a valve cycle, and ranges generally from about 35 to about 200 seconds. A typical process contains from 8 to 24 adsorbent sub-beds, an equal number of distributors located between the each adsorbent sub-bed, two liquid input lines, two liquid output lines, and associated flush lines.

The principal liquid inputs and outputs of the adsorbent system consists of four streams: the feed mixture, the extract, the raffinate, and the desorbent. Each stream flows into or out of the adsorbent system at a particular flow rate, and each flow rate is independently controlled. The feed, which is introduced to the adsorbent system, contains the component or group of components which are to be separated from other components in the feed stream. The desorbent, which is introduced to the adsorbent system, contains a liquid capable of displacing feed components from the adsorbent. The extract, which is withdrawn from the adsorbent system, contains the separated component which was selectively adsorbed by the adsorbent, and desorbent liquid. The raffinate, which is withdrawn from the adsorbent system, contains the rest of the feed components which were less selectively absorbed by the adsorbent, and desorbent liquid. There also may be associated flush streams introduced to and withdrawn from the adsorbent system. The four principal streams are spaced strategically throughout the adsorbent system and divide the sub-beds into four zones, each of which performs a different function.

Zone I contains the adsorbent sub-beds located between the feed input and the raffinate output, and adsorption of the component of interest takes place in this zone. Zone II contains the adsorbent sub-beds located between the extract output and the feed input, and the desorption of components other than those of interest takes place in this zone. Zone III contains the adsorbent sub-beds located between the desorbent input and the extract output, and the component of interest is desorbed in this zone. Finally, Zone IV contains the adsorbent sub-beds located between the raffinate output and the desorbent input, and the purpose of this zone is to prevent the contamination of the component of interest with other components.

The other two important separation process streams for the purpose of this invention are the pumparound and pusharound streams. In typical separation processes the adsorbent beds are housed in chambers; usually ranging from 1 to 24 or more chambers. For example, if the separation process contains 24 sub beds which are split into two chambers, one chamber would contain sub-beds 1 through 12 and the other would contain sub-beds 13 through 24. Although functionally the adsorbent system as a whole does not have a top or a bottom, each chamber has a physical top and bottom. The pumparound and pusharound streams each conduct the liquid effluent exiting the physical bottom of one adsorbent bed chamber back up to reenter the physical top of the other adsorbent bed chamber. In the 24 sub-bed example, the pumparound stream would be the stream that conducts the effluent of sub-bed 24 from the physical bottom of the second chamber to reenter sub-bed 1 at the physical top of the first chamber, and the pusharound stream would conduct the effluent of sub-bed 12 from the physical bottom of the first chamber to reenter sub-bed 13 at the physical top of the second chamber. It may be possible, however, that the separation process contains only one adsorbent chamber and has only a pumparound stream. It is important to note that the composition of the pumparound or pusharound stream changes with each valve step, and in one valve cycle both streams will have sequentially carried the composition which corresponds to each valve position.

The foregoing is a brief description of relevant portions of the a separation process; for a more detailed explanation, see Mowry, J. R. In *Handbook of Petroleum Refining Processes;* Meyers, R. A. Ed.; McGraw-Hill: New York, 1986; pp 8–79 to 8–99. For greater detail regarding the simulated moving bed and its operation, see U.S. Pat. No. 2,985,589.

The common practice in industry is to control separation processes either by on-line gas chromatography analyses, or by off-line laboratory analyses. When controlling on-line, the gas chromatography analysis of the pumparound stream generally requires about 10 minutes which is considerably greater than the usual step time of the rotary valve. Therefore, only select valve positions may be sampled and analyzed. Generally, only Zone II near the extract output and Zone IV near the desorbent input are sampled and analyzed. The data provided by this on-line gas chromatography procedure is useful for detecting process upsets, but unfortunately analyzing the composition of only two valve positions provides limited information regarding the performance of the separation process and is only minimally useful for precise separation process control.

A more thorough control is accomplished using off-line laboratory gas chromatography or high performance liquid chromatography analyses to determine the values of the concentrations of the components in samples of the pumparound stream taken at each valve position in a valve cycle. The measured concentrations are then plotted versus their relative valve positions to form what is generally called a profile. Using the profile, the recovery and purity of the component of interest can be calculated and the degree of optimization of the separation assessed. Then required changes in the step time and liquid stream flow rates may be determined and implemented. The drawbacks to controlling a separation process in this fashion are the time delay between sampling and analytical results where the latter are used to determine whether or what changes should be made, the labor involved to manually collect the stream samples, and the personal exposure of the operator manually collecting the stream samples. Since the analyses are performed off-line, the time delay may be from one to several days long. Because of the drawbacks, refiners generally only perform this procedure about once every six months or if there is a problem with the separation process.

Other separation processes have been controlled using spectroscopic determinations of impurities in the separated pure product. For instance the Canadian Patent Application 2,050,108 discloses spectroscopically measuring one component of a mixture in another component of the mixture following the separation of the mixture into its components. The results of the measurements are used to control the separation so that the amount of impurity in the pure product is controlled to a desired value.

The present invention moves beyond the current practice and discloses a more useful process of control through conveniently providing the necessary quantity of information for precise process control in a far more beneficial time frame. Specifically, the present invention allows for on-line virtually instantaneous measurements of the values of the components at each valve position, which in turn allows a complete profile of the separation to be generated in one valve cycle. Adjustments to the separation process may then be timely made, and the para-xylene purity and/or recovery may be controlled with efficiency, precision, and accuracy. Furthermore, the control process may be fully automated so that the greatest amount of information is timely and conveniently available.

SUMMARY OF THE INVENTION

The purpose of this invention is to provide a process of continuously controlling at least one characteristic of a separation process. An embodiment comprises controlling the separation to either achieve a target value of the characteristic, or to maximize the value of the characteristic. In a more specific embodiment the invention uses the concentrations of the components in the pumparound or pusharound stream measured at three or more valve positions to control a characteristic of the separation process. In a still more specific embodiment the concentration of the components are measured using either near infrared spectroscopy or mid-range Fourier-transform infrared spectroscopy. In another embodiment spectroscopic measurements are performed either on-line or in-line. In yet another specific embodiment of the invention the characteristic controlled is the purity of the product. Another specific embodiment is one where the characteristic controlled is the recovery of the component of interest by the separation process.

BRIEF DESCRIPTION OF THE DRAWING

The drawing is a schematic representation of a generic simulated moving adsorbent bed para-xylene separation process, modified and operated in accordance with the process of this invention. The drawing has been simplified by the deletion of a large number of pieces of apparatus customarily employed on a process of this nature which are not specifically required to illustrate the performance of the subject invention.

DETAILED DESCRIPTION OF THE INVENTION

The invention is the process of continuously controlling at least one characteristic of a separation process containing a simulated moving adsorbent bed. In general terms, the characteristic, which has an initial value, $V_I$, a target or desired value, $V_T$, and an allowable variance from the target value, $\delta$, is controlled through measuring the concentrations of the components in the pumparound or pusharound stream at three or more valve positions of the rotary valve, and determining the necessary changes in the values of the step time and liquid stream flow rates in order to achieve the target value of the characteristic by applying a suitable algorithm to the values either manually or with the aid of a computer. The liquid streams whose flow rates may be adjusted are primarily the feed stream, the extract stream, the raffinate stream, and the desorbent stream. The flow rates of the associated flush streams may be adjusted for a secondary control. The components whose concentrations are measured are generally the component of interest and the other major components of the mixture. For example in the separation of para-xylene from other xylene isomers the components measured may be para-xylene, meta-xylene, ortho-xylene and ethylbenzene. The algorithm relates changes in the value of the characteristic to changes in the step time and flow rates with resulting changes in the values of the concentrations of the components at each valve position measured. Applying an algorithm determines the required changes in the step time and flow rates to produce a new value of the characteristic, $V_N$, which is numerically closer to the target value. This progression can be represented as $|V_T-V_N| \leq |V_T-V_I|$. The step time and flow rates are then adjusted as required, preferably automatically, and the control process is repeated until the value of the characteristic is within the allowable variance of the target value, which can be represented as $|V_T-V_N| \leq \delta$. It is important to note that while it is preferred to adjust the flow rates and the step time, it is not necessary to adjust both. It is possible to adjust only the step time, or only the flow rates and still control the characteristic.

The characteristics controlled are generally the purity of the product in the extract stream and the recovery of component of interest from feed into the product extract. The characteristics may be either measured or calculated. The preferred embodiment is to calculate the theoretical values of the characteristics from the measurements of the concentrations of the components since the actual measurements may involve variables introduced at locations other than in the actual separation. Such calculations are common, and are generally known to those skilled in the art. Either the purity or the recovery may be controlled, or both may be controlled simultaneously, and, as discussed earlier, the control may be to achieve either a target value of the characteristic or to maximize the value of the characteristic.

The pumparound and pusharound streams are the preferred locations to perform the measurements of the concentrations of components since with every step of the rotary valve, these streams carry a new composition corresponding to the relative position of the valve. In one complete valve cycle the stream will have sequentially carried the composition corresponding to each relative position of the valve. When both streams are present in the separation process, generally only one stream, either the pumparound or the pusharound, is measured. Which is chosen is not important to the success of the invention and the choice may be based on convenience. Once the choice is made, however, the chosen stream must be used for at least one complete valve cycle.

The components whose concentrations are measured in the pumparound or pusharound stream are those which are necessary to calculate the characteristic of interest. At the minimum, at least the concentration of the component of interest must be measured. Usually, the concentration of the component of interest and the major contaminants are measured. However, if desired, the concentrations of all the components may be measured. How many concentrations are measured depends upon the application and is readily determined by one skilled in the art.

The concentrations of the components in the pumparound and pusharound streams can be measured by any suitable analytical technique whose analysis time is less than the step time of the rotary valve, generally about 60 to 90 seconds. The preferred analytical technique is spectroscopy. While mid-range Fourier-transform infrared spectroscopy (FT-IR) is suitable, near infrared spectroscopy (NIR) is the most preferred spectroscopic technique. Spectroscopic determinations of the values of the concentrations of the components in the pumparound or pusharound stream pursuant to this invention are made by first measuring the absorption, reflectance, or transmission spectrum of the pumparound or pusharound stream and then calculating the values of said concentrations according to a predetermined algorithm relating said concentrations of said components to the spectrum. The wavelength range over which the spectrum is measured varies depending on the separation process and the components being measured. For example, for the separation of para-xylene from other xylene isomers where the components being measured are para-xylene, meta-xylene, ortho-xylene and ethylbenzene, the spectrum may be obtained over the range of about 700 to about 2,500 nm, or preferably about 1,100 to about 1,700 nm when using NIR and over the range of about 2.5 to about 25 µm, and especially the range of about 7.5 to about 15 µm, when using FT-IR. Such optical measurements are known in the art, as are several mathematical algorithms for analyzing the spectral data including but not limited to, partial least squares with latent variables, multiple linear regression, and principal component regression. See generally, Martens, H.; Naes, T. *In Multivariate Calibration by Data Compression;* Williams, P.; Norris, K. Eds.; Near Infrared Technology in the Agricultural and Food Industries; Amer. Assoc. Cereal Chemists: St. Paul; Chapter 4. Applying NIR or FT-IR spectroscopy contributes to the superior efficiency of the invention since the techniques require no sample preparation, and are accurate, rapid and non-destructive. Furthermore, the spectroscopy can be performed on-line, where the sample is automatically routed from the pumparound or pusharound stream to the spectrophotometer, or in-line, where a probe is placed directly in the pumparound or pusharound stream. The data is available in less than a minute, which when used in the present invention translates into the ability to immediately and precisely control the value of a characteristic.

The preferred embodiment of the invention is that where the concentration of the components in the pumparound or pusharound stream are measured at every valve position. As is commonly known by those skilled in that art, random noise in spectroscopy measurements may be reduced by repeatedly measuring the spectrum and performing spectral averaging. Therefore, to increase the precision of the measurements, this invention embodies the situation where the set of concentrations of components corresponding to a given valve position is the average of repeated measurements made while the valve was in that position. The plurality of measurements are preferably made on the dynamic flowing pumparound or pusharound stream so that the average represents the average concentrations of the components over the duration of the valve step. It is further understood that, where appropriate, the measurements of the dynamic flowing stream within one valve step may be used to determine the profile of the concentrations of the components over the duration of the valve step instead of being averaged. It is also contemplated that a static sample from the pumparound or pusharound stream contained in a suitable sample cell could be measured repeatedly and averaged. The results of the static measurements would be particular to one point within the valve step, as opposed to an average over the duration of the valve step.

How many measurements may be taken within a valve step depends upon the speed of the analyzer and the step time of the rotary valve. For example, if the step time is 60 seconds, and the analysis time for the spectroscopy measurement is 6 seconds, a maximum of 10 spectra may be measured before the valve advances. If the maximum number of measurements possible within the step time provides insufficient precision, a static sample may be used, and the number of measurements may be increased. The consequence, however, is that under these circumstances not every valve position may be measured. For purposes of this invention, the minimum number of valve positions for which measurements are required is three.

In the preferred embodiment where the values of the concentrations of the components are measured at each valve step, the results of the measurements may be plotted versus the relative positions of the valve to generate a profile. While generating such a profile is not necessary, it does provide additional advantages. By inspecting the profile, an operator may be able to learn troubleshooting information such as whether there has been a process upset, the adsorbent has been poisoned, or whether the degree of adsorbent hydration is correct. As the number of valve positions measured decreases from the preferred, the profile may still be plotted, but it becomes less useful and less information such as described above may be obtained.

Once the values of the concentrations of the components in the pumparound or pusharound stream for one valve cycle have been collected, a suitable algorithm may be applied to determine the required changes in the step time and liquid stream flow rates to effect a desired change in the characteristic controlled. Suitable algorithms may be any of those commonly used including multivariate regression and neural network modeling. The preferred algorithm is multivariate regression. The algorithm may be applied manually or preferably with the aid of a computer.

The step time and liquid stream flow rates are then adjusted as required. The required adjustments may be in any combination. For example, only one liquid stream flow rate may be adjusted, all four principal streams may be adjusted, or any group of two or three may be adjusted. Furthermore, the direction and degree of adjustment required for each stream flow rate may be different. For example, while one flow rate may be increased substantially, another flow rate may be slightly decreased. Also, the combination of flow rate adjustments may be accompanied by a step time adjustment, or the step time adjustment maybe made with no flow rate adjustments. The step time may be adjusted to a longer time or to a shorter time. Very often, one variable may be adjusted to a required new value, and as a consequence others may be changed in order to keep various process conditions constant.

The adjustments may be made manually, or automatically. The preferred method is to perform the adjustments automatically. The entire control procedure may then be repeated. After the target value of the characteristic has been achieved or the value of the characteristic has been maximized, the control process may be repeated periodically to monitor the characteristic.

Without intending any limitation on the scope of the present invention, and as merely illustrative, this invention is explained below in specific terms as applied to one embodiment of controlling the recovery of para-xylene from a feed stream containing para-xylene, meta-xylene, ortho-xylene and ethylbenzene. The necessary apparatus is first described, and then process of the invention as applied to the embodiment is discussed. For ease of understanding, the process of the invention is described below as the control of the value of only one characteristic, the recovery, and the variation of only one set of variables, the flow rates of the principal streams.

Turning now to the apparatus as illustrated in the drawing, distribution lines 1–12 are available to conduct liquid streams to or from the first adsorbent chamber 25. Similarly, distribution lines 13–24 are available to conduct liquid streams to or from the second adsorbent chamber 26. All of the distribution lines 1–24 are also connected to a rotary valve 29. The rotary valve 29 is further connected to line 30 which conducts the feed to the valve, line 31 which conducts raffinate away from the valve, line 32 which conducts desorbent to the valve, and line 33 which conducts extract away from the valve. Each of the lines 30–33 is provided with a flow rate sensor and flow control valve respectively indicated at 34–37.

The line 28 conducts the effluent, or pusharound stream, from the bottom of the first adsorbent chamber 25 to the top of the second adsorbent chamber 26. The line 27 conducts the effluent, or pumparound stream, from the bottom of the second adsorbent chamber 26 to the top of the first adsorbent chamber 25. The line 27 is provided with an optical sampling interface 38 that is coupled to a spectrophotometer 40 by a fiber optic cable 39. The spectrophotometer is coupled by a data bus 41 to a computer 42. The rotary valve 29 and each of the flow rate sensors and flow control valves 34–37 are similarly respectively coupled to the computer 42 via data buses 43–47.

Using the described apparatus, the invention is performed as follows. The flow rates of each of the lines 30–33 and the step time of the rotary valve 29 may be first set to selected values based on the operator's experience. The starting position of the rotary valve is not important; for this illustration the starting position of the rotary valve is such that the desorbent is directed to the first adsorbent chamber 25 through distribution line 3, the extract is directed from the first adsorbent chamber 25 through distribution line 9, the feed is directed to the second adsorbent chamber 26 through distribution line 17, and the raffinate is directed from the second adsorbent chamber 26 through distribution line 24.

While at this starting valve position, and during the first step time, the concentrations of para-xylene, ethylbenzene, ortho-xylene, and meta-xylene in the pumparound stream flowing through line 27 are measured by repeatedly measuring the NIR spectrum of the pumparound stream over the range of 1,100 to 1,700 nm using the optical sampling interface 38, fiber optic cable 39 and the spectrophotometer 40. The spectra are then electronically conducted through data bus 41 to the computer 42 where they are analyzed according to a suitable mathematical technique, e.g., partial least squares with latent variables. The results are averaged to produce an average concentration value for each component at the starting valve position, and the values are stored in the computer 42.

When the step time has elapsed, the rotary valve 29 advances one index and now directs the desorbent through distribution line 4, the extract through distribution line 10, the feed through distribution line 18, and the raffinate through distribution line 1. Again the concentrations of para-xylene, ethylbenzene, ortho-xylene, and meta-xylene flowing through the pumparound line 27 are measured as described above. The measurements are performed during the step time following each advancement of the rotary valve until the valve has completed one cycle.

Using the gathered data and commonly known formulas, the value of the recovery of the product para-xylene is then calculated using the computer 42. The flow rate of one or more streams are then varied by adjusting the associated flow controller. The measurements of the concentrations are then performed as discussed above during each step time of another valve cycle. Again the value of the recovery is calculated using the newly gathered data.

A suitable algorithm, such as multivariate regression, which relates the changes in the flow rates to the changes in the value of the recovery is then applied. The algorithm is used to determine the required changes in the flow rates of the streams to afford a recovery whose value is numerically closer to the target value. The required changes are implemented via signals generated by the computer 42 which are transported through data buses 44–47 to the flow controllers 34–37 resulting in the required adjustments of the flow controllers. The foregoing procedure of 1) measuring the concentrations of the pumparound stream at each valve position of a valve cycle; 2) calculating the recovery; 3) applying an algorithm to determine the required changes in the flow rates of the streams; and 4) implementing the required flow rate changes; is then repeated until the value of the recovery is within an acceptable range of the target value.

It must be emphasized that the above description is merely illustrative of a preferred embodiment, and is not intended as an undue limitation on the generally broad scope of the invention. Moreover, while the description is narrow in scope, one skilled in the art will understand how to extrapolate to the broader scope of the invention. For example, the procedure for the simultaneous control of more than one characteristic can be readily extrapolated from the foregoing description. Similarly, one skilled in the art would understand how both the step time and the flow rates of the streams might be adjusted. One skilled in the art would also readily recognize how to apply the invention to additional separation processes.

What is claimed is:

1. A process of continuously controlling the value of a characteristic of a simulated moving adsorbent bed separation, said characteristic selected from the group consisting of purity of a product stream, recovery of at least one component, and the combination thereof, said simulated moving adsorbent bed separation having multiple input and output streams each with individual flow rates, a step time, multiple valve positions, and at least one component in pumparound or pusharound streams, where the initial value of the characteristic is $V_I$, and the final value of the characteristic is to be within $\pm\delta$ of a target value $V_T$, said process comprising:

a. determining the concentration of at least one component in said pumparound or pusharound stream at a minimum of three valve positions within one valve cycle;

b. determining the value of the characteristic using the aggregate of concentrations determined within one valve cycle;

c. adjusting the step time and flow rates according to an algorithm, selected from the group consisting of multivariate regression and neural network modeling, said algorithm relating the changes in the value of characteristic to changes in the step time and flow rates with resulting changes in the value of the concentration of the component at each valve position measured, to afford a new value of the characteristic, $V_N$, where $|V_T-V_N| \leq |V_T-V_I|$; and d. repeating steps (a) through (c) until $|V_T-V_N| \leq \delta$.

2. The process of claim 1 where the value of the concentration of the component in the pumparound or pusharound stream is determined on-line.

3. The process of claim 1 where the value of the concentration of the component in the pumparound or pusharound stream is determined in-line.

4. The process of claim 1 where the value of the concentration of the component in the pumparound or pusharound stream is determined at each valve position.

5. The process of claim 1 where multivariate regression is the mathematical technique used in said algorithm.

6. The process of claim 1 where said simulated moving adsorbent bed separation is selected from the group consisting of the separation of para-xylene from xylene isomers, the separation of linear paraffins from branched-chain and the separation of cyclic hydrocarbons and olefins from paraffins.

7. The process of claim 1 where the value of the concentration of the component in the pumparound or pusharound stream is determined by mid-range Fourier-transform infrared spectroscopy.

8. The process of claim 1 where the value of the concentration of the component in the pumparound or pusharound stream is determined by near infrared spectroscopy.

* * * * *